United States Patent [19]

Enders

[11] 4,148,799
[45] Apr. 10, 1979

[54] PROCESS FOR THE PREPARATION OF 2-ARYLIMINOTHIAZOLINE SOLUTIONS

[75] Inventor: Edgar Enders, Cologne, Fed. Rep. of Germany

[73] Assignee: Bayer Aktiengesellschaft, Leverkusen, Fed. Rep. of Germany

[21] Appl. No.: 797,728

[22] Filed: May 17, 1977

[30] Foreign Application Priority Data

May 21, 1976 [DE] Fed. Rep. of Germany ....... 2622949

[51] Int. Cl.$^2$ .......................................... C07D 277/42
[52] U.S. Cl. .............................. 260/306.7 T; 424/270
[58] Field of Search .................................. 260/306.7 T

[56] References Cited

U.S. PATENT DOCUMENTS 3,804,848  4/1974  Behner et al. ................. 260/306.7 T

FOREIGN PATENT DOCUMENTS 627278  7/1963  Belgium ............................ 260/306.7 T
1218210         Fed. Rep. of Germany.

*Primary Examiner*—Paul M. Coughlan, Jr.
*Attorney, Agent, or Firm*—Sprung, Felfe, Horn, Lynch & Kramer

[57] ABSTRACT

Certain new 2-aryliminothiazolines which can optionally be ring-alkylated are provided and, particularly, a new process is provided for the preparation of solutions of said 2-aryliminothiazolines. The 2-aryliminothiazoline solutions obtained are of about 10–80% strength, preferably about 20–70% strength and can be used as such or diluted and used, for example, as tickicidal agents.

5 Claims, No Drawings

PROCESS FOR THE PREPARATION OF 2-ARYLIMINOTHIAZOLINE SOLUTIONS

The present invention relates to a new process for the preparation of solutions of 2-aryliminothiazolines, some of which compounds are known, and to the solutions obtained by means of this new process.

2-Aryliminothiazolines of the general formula

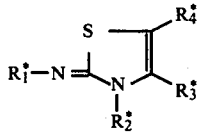

in which
  $R^*_1$ represents, inter alia, an optionally substituted phenyl radical,
  $R^*_2$ represents, inter alia, hydrogen or alkyl ($C_1$–$C_3$),
  $R^*_3$ represents, inter alia, hydrogen and
  $R^*_4$ represents, inter alia, hydrogen,
and their use as fungicidal agents having an additional herbicidal and nematocidal action have already been disclosed (compare German Auslegeschrift (German Published Specification) No. 1,218,210).

Furthermore, it has been disclosed in DT-AS (German Published Specification) No. 1,218,210 that the abovementioned 2-iminothiazolines can be prepared either by
(a) reacting a monosubstituted thiourea with an α-halogenocarbonyl compound and subsequently alkylating, if appropriate, the reaction product or
(b) reacting a N,N'-disubstituted thiourea with an α-halogenocarbonyl compound.

The synthesis of 2-iminothiazolines by reaction of phenylthiourea or p-chlorophenylthiourea with chloroacetone and of N,N'-diphenylthiourea with chloroacetone and of N,N'-diphenylthiourea with phenacyl bromide have already been described earlier.

The reaction of thiourea with α,β-dichlorodiethyl ether to give 2-aminothiazole or 2-imino-1,3-thiazoline is also known. For summary see T. S. Griffin et al., "Thioureas in the Synthesis of Heterocycles" in Advances in Heterocycl. Chem. Vol. 18, page 109 et seq. (1975).

The processes, which have been disclosed, for the preparation of 2-aryliminothiazolines are carried out in two stages. In the first stage, arylamines Ar-NH$_2$ are reacted with thiocyanic acid or alkylisothiocyanates R$_1$-NCS or, alternatively, arylisothiocyanates Ar-NCS are reacted with ammonia or alkylamines R$_1$-NH$_2$ to give thioureas of the formula

wherein
  Ar represents optionally substituted aryl and
  R$_1$ represents hydrogen or alkyl ($C_1$–$C_4$).

In the second stage the isolated thioureas II are then reacted with 2-halogeno-carbonyl compounds III

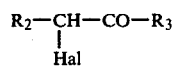

wherein
  R$_2$ and R$_3$ represent hydrogen or alkyl ($C_1$–$C_4$) and
  Hal represents chlorine or bromine, or acetal derivatives of the 2-halogeno-carbonyl compounds III to give 2-arylimino-thiazolines of the general formula I which, in the known processes, must again be isolated and purified. The resulting compounds of the general formula

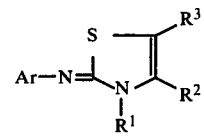

in which
  Ar, R$^1$, R$^2$ and R$^3$ have the meaning indicated above, exhibit a very good ectoparasiticidal, and especially tickicidal, action.

In the processes known hitherto, predominantly water-soluble solvents, such as, for example, acetone or ethanol, used in the two reaction stages. In addition, the use of non-polar solvents, and preferably of toluene, as the reaction medium is proposed in DT-AS (German Published Specification) No. 1,218,210.

For industrial purposes, various disadvantages are associated with the known processes. The intermediate isolation of the thioureas II and the renewed employment for the preparation of the 2-arylimino-thiazolines of the general formula I is an expensive procedure which is subject to the disadvantages of necessitating working up of the solvent used by distillation, losses of solvents and effluent problems. Thereafter, for the further processing of the 2-aryliminothiazolines I to ectoparasiticidal formulations which are ready for application solvents, which must fulfill specific requirements, must again be added. The solvents contained in the formulations which are ready for application should have as low a volatility as possible so that when the formulations are used in open animal baths (dip) the solvent constituent does not evaporate and so that the fine distribution and/or redispersibility of the active compound remains guaranteed even after a relatively long standing time. When changes occur in the relative concentrations of active compound, solvent and further dispersing agents and emulsifying agents which are added, this requirement is jeopardised.

In addition, the solvents used must be well tolerated by the skin and also, in the case of open wounds and inflammatory changes of the skin, they must not lead to pain reactions in the treated warm blooded animals such as cattle or sheep. Further requirements of the solvent to be used are non-toxicity, low inflammability, no odour or only a slight odour and a low melting point (below 20° C.).

It has not been found that the abovementioned disadvantages of the processes, which have been disclosed hitherto, for the preparation of solutions of the 2-aryliminothiazolidines, some of which compounds are known, of the general formula I

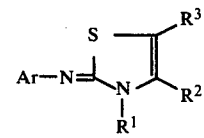

in which

Ar represents an optionally substituted phenyl or naphthyl radical and

R¹, R² and R³ independently of one another represent hydrogen or alkyl (C₁–C₄), can be avoided either if an arylamine of the formula Ar-NH₂ in which Ar has the meaning indicated above, is reacted with a compound of the formula

R¹—NCS in which

R¹ represents hydrogen or alkyl (C₁–C₄), and the thiourea intermediate product formed is then reacted, without isolation, with a halogenocarbonyl compound of the formula

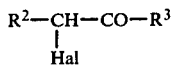

R²—CH—CO—R³     III
    |
    Hal in which

R² and R³ have the meaning indicated above and

Hal represents halogen, or with an acetal derivative of the abovementioned halogenocarbonyl compound, the reaction sequence being carried out in an aromatic solvent of the benzene or naphthalene series (boiling range 130°–400° C.), optionally in a mixture with further solvents, at temperatures between about 20° and about 120° C., or if an aryl isocyanate of the formula Ar—NCS in which Ar has the meaning indicated above, is reacted with a compound of the formula

R¹—NH₂ in which

R¹ represents hydrogen or alkyl (C₁–C₄), and the thiourea intermediate product is then reacted, without isolation, with a halogenocarbonyl compound of the formula

R²—CH—CO—R³     III
    |
    Hal in which

R² and R³ have the meaning indicated above and

Hal represents halogen, or with an acetal derivative of the abovementioned halogenocarbonyl compound, the reaction sequence being carried out in an aromatic solvent of the benzene or naphthalene series (boiling range 130°–400° C.), optionally in a mixture with further solvents, at temperatures between about 20° and about 120° C.

It is to be described as decidedly surprising that the reaction according to the invention proceeds so smoothly in the solvents used, since the substances formed transiently as intermediate products in the reaction according to the invention (N-arylthioureas or N-aryl-N'-alkylthioureas) are sparingly soluble in the solvents used and in general crystallise out quantitatively.

In the course of the further reaction with, for example, aqueous chloroacetaldehyde solutions, a three-phase system forms, consisting of organic solvent, aqueous solution and sparingly soluble thiourea, which has precipitated in the crystalline form. In spite of the formation of this heterogeneous three-phase system, a smooth reaction takes place, surprisingly and contrary to general experience,, with the formation of the 2-arylimino-thiazolines of the general formula I in high yield (in general greater than 90% of theory).

The process, according to the invention, for the preparation of the thiazolines of the formula I does not have the disadvantages described above of the processes, which have been disclosed hitherto, for the preparation of solutions of the 2-arylimino-thiazolines of the formula I. By appropriate metering of the starting products and solvent amounts it is possible, with the aid of the process according to the invention, to obtain 10–80% strength, preferably 20–70% strength, solutions of the 2-arylimino-thiazolines of the general formula I which can be used either directly as ectoparasiticidal, and especially tickicidal, agents or, by adding formulation auxiliaries, such as, for example, emulsifiers and/or wetting agents, in ready-to-use ectoparasiticidal, and especially tickicidal, agents, in particular for employment in animal dips.

If 4-amino-1,3-dimethyl-benzene, methyl isothiocyanate and chloroacetaldehyde are used as the reactants for carrying out the reaction according to the invention, the course of the reaction according to the invention can be illustrated by the following equation:

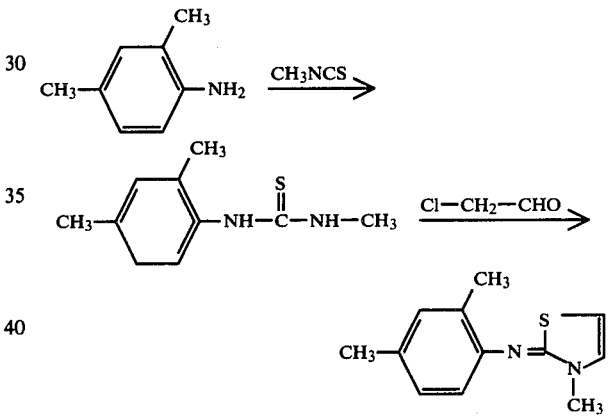

If 2,4-dimethyl-phenyl isothiocyanate, methylamine and chloroacetaldehyde are used as the reactants, the reaction according to the invention can be illustrated as follows:

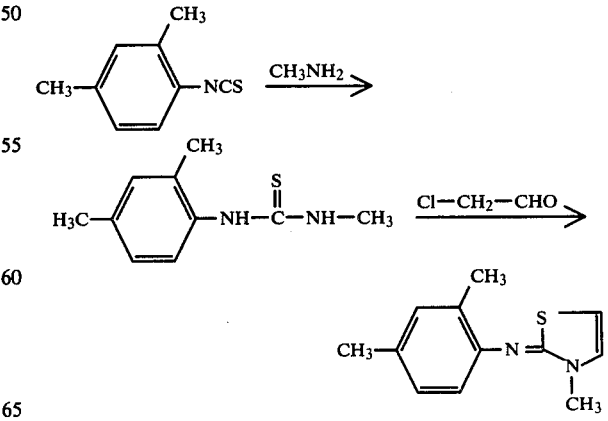

In the formula I, Ar preferably represents phenyl, which can be substituted by the following radicals:

alkyl (C₁–C₄; halogen, in particular fluorine, chlorine and bromine; trifluoromethyl, amino, dialkylamino (C₁–C₄) per alkyl group, acylamino (C₁–C₄) and alkoxycarbonylamino (C₁–C₄); cycloalkyl (C₃–C₆), in particular cyclopentyl and cyclohexyl; alkoxy (C₁–C₄), in particular methoxy and ethoxy; phenyl, phenoxy, alkylsulphonyl (C₁–C₄), in particular methylsulphonyl and ethylsulphonyl, nitro, cyano and alkenoyl (C₁–C₄) in particular acetyl and optionally further substituents.

The number of substituents on the radical Ar is 0 to 5, preferably 0 to 3.

The radicals $R^1$, $R^2$ and $R^3$ represent, in particular, hydrogen, methyl and ethyl.

As already mentioned above, solvents which can be used in the reaction according to the invention are solvents which, after carrying out the reaction, can subsequently be used as formulation auxiliaries and diluents.

According to the invention, aromatic solvents of the benzene or naphthalene series having boiling points within the range from 130°–400° C., preferably 150°–350° C., are used here. Suitable solvents which may be mentioned are: ortho-, meta- and para-xylene or mixtures of these, ethylbenzene, isopropylbenzene, tert.-butylbenzene, dodecylbenzene, 1,3-diethylbenzene, 4-isopropyl-toluene, 1,2,4- and 1,3,5-triisopropyl-benzene, mesitylene, acetophenone, anisole, phenetole, chlorobenzene, 1,2- and 1,3-dichlorobenzene, also in a mixture with 1,4-dichlorobenzene; mixtures of diphenyl ether and biphenyl, in particular the eutectic mixture; dimethyl phthalate and diethyl phthalate; 1-methylnaphthalene, also in a mixture with 2-methylnaphthalene and/or dimethylnaphthalenes; and 1-isopropylnaphthalene, 2-isopropylnaphthalene, 1-chloronaphthalene and 1-naphthyl methyl ether.

The solvents mentioned can optionally also be present in a mixture with one another or with further solvents, in particular also with aliphatic hydrocarbons in the boiling range claimed according to the invention. The limiting characteristic for the admixing of aliphatic hydrocarbons is the low solubility of 2-aryl-imino-thiazolines in aliphatic hydrocarbons.

The boiling ranges of the solvent mixtures which can be used according to the invention can vary within the limits indicated, that is to say from 130°–400° C., preferably from 150°–350° C., as can be the case in industrial mixtures, for example in alkylnaphthalene and alkylbenzene fractions having an average boiling point of 230° C. and a boiling range from 180°–280° C.

According to the invention, the solvents described above are employed in the synthesis of the 2-arylimino-thiazolines I in such an amount that, after carrying out the reaction sequence, 10–80% strength, preferably 20–70% strength, solutions of the reaction product in the solvent used are present.

For this purpose, for example, 4-amino-1,3-dimethylbenzene is initially introduced in the amount by weight of an alkyl-benzene and -naphthalene mixture, having a boiling range of 180°–280° C., calculated for a final concentration of I of 46% and the calculated amount of methyl isothiocyanate is allowed to run in at 40°–80° C. The conversion to the sparingly soluble, crystalline N-(2,4-dimethyl-phenyl)-N'-methyl-thiourea III takes place in an exothermic reaction. The calculated amount of a 45% strength aqueous chloroacetaldehyde solution is added dropwise to the concentrated suspension of the thiourea at 40°–80° C. The thiourea gradually goes into solution and an emulsion of an organic and an aqueous phase forms. After the reaction has ended, the thiazoline base is liberated from the hydrochloride formed of the thiazoline derivative by adding a base, for example sodium carbonate solution or aqueous sodium hydroxide solution, the aqueous layer is separated off and the solvent phase is dried either by stirring with a drying agent, such as, for example, potassium carbonate, and filtration or by warming in vacuo.

In the reaction sequence described above by way of example a 46% strength solution of the tickicidal active compound 2-(2,4-dimethylphenyl-imino)-3-methyl-thiazoline is directly obtained, which can be directly converted into a 30% strength ectoparasiticidal formulation, which is ready for application, by adding 54% by weight of an emulsifier (for example an alkylphenol-/ethylene oxide condensation product).

Alternatively, in the reaction according to the invention for the preparation of the solution of the tickicidal active compound 2-(2,4-dimethylphenylimino)-3-methylthiazoline, it is also possible to react 2,4-dimethylphenyl isothiocyanate with methylamine to give the same intermediate product N-(2,4-dimethylphenyl)-N'-methylthiourea, which is not isolated, either by passing in methylamine gas or by stirring an aqueous 40% strength methylamine solution with a solution of 2,4-dimethylphenyl isothiocyanate in the abovementioned alkylbenzene mixture.

By the limitation on the solvent to be used according to the invention, imposed at times in the process according to the invention, to those amounts which give, after the synthesis has been carried out, about 10–80% strength, preferably about 20–70% strength, solutions of the 2-arylimino-thiazoline I, the stirrability of the thiourea suspensions (II) obtained as the intermediate product can at times be jeopardised, especially in higher concentration ranges (50–80% strength).

According to the invention, therefore, solvents which are immiscible with water and which have boiling points below 100° C. can be added to the mixtures. The amount of solvent to be added is calculated so that the stirrability of the suspension and thus the processability remains guaranteed.

Suitable solvents are, for example, benzene, cyclohexane, methylcyclohexane, cyclohexene, ethyl acetate, carbon tetrachloride, chloroform and aliphatic fractions having a boiling range from 50°–100° C., for example 60°–80° C. In general, the addition is 30–300% by volume, preferably 50–200% by volume, relative to the volume of the main solvent. After the reaction sequence has been carried out and the aqueous phase is separated off, the auxiliary solvent is again distilled off, drying of the active compound solution proceeding simultaneously by means of azeotropic removal of residual moisture.

Arylamines of the general formula

which can be used in carrying out the reaction according to the invention are, preferably, aniline and aniline derivatives which are substituted in the aryl radical, preferably by alkyl radicals and/or halogen atoms. Examples which may be mentioned are: 2-methylaniline, 4-methylaniline, 2,4-dimethylaniline, 2,3- and 2,6-dimethylaniline, 2-methyl-4-ethyl-aniline, 4-methyl-2-ethylaniline, 2-methyl-3-ethylaniline, 3-methyl-2-ethylaniline, 2-ethylaniline, 2,4- and 2,6-diethyl-aniline, 2,4,5-, 2,3,4-, 2,4,6- and 2,3,6-trimethylaniline, 2-isopropylaniline, 2-methyl-4-isopropylaniline, 2-ethyl-4,5- dimethylaniline, 2-cyclopentylaniline, 2- and 4-chloroaniline, 4-bromoaniline, 2,4-, 3,4-, 2,3- and 2,6-dichloroaniline, 2,4,5- and 2,4,6-trichloroaniline, pentachloroaniline, 2-chloro-4-fluoroaniline, 2-chloro-4-bromoaniline, 2-methyl-4-chloroaniline, 3-chloro-4-methylaniline, 4-chloro-3-methylaniline, 2-methyl-4-bromoaniline, 2-chloro-3-methylaniline, 2-chloro-6-methylaniline, 3-chloro-2-methylaniline, 4-chloro-2,3-dimethylaniline, 4-chloro-2,5-dimethylaniline, 5-chloro-2,4-dimethylaniline, 2-chloro-4-trifluoromethylaniline, 4-chloro-2-trifluoromethylaniline, 2-chloro-5-trifluoromethylaniline, 3,5-bis-trifluoromethylaniline and 4-trifluoromethylaniline.

Further aniline derivatives which may be mentioned are: 2-chloro-4-nitroaniline, 2-chloro-4-acetylaminoaniline, 4-aminophenyl, 2-chloro-4-methoxyaniline, 2-methyl-4-methoxyaniline, 2,4-dimethoxyaniline, 4-aminobiphenyl, 3-chloro-4-aminobiphenyl, 4-amino-4'-chloro-diphenyl ether, 4-amino-2,6,4'-trichloro-diphenyl ether, 4-amino-dimethylaniline, 3-chloro-4-amino-dimethylaniline and 4-methylsulphonyl-2-chloroaniline.

Naphthalene derivatives which may be mentioned are: 1-amino-naphthalene, 1-chloro-2-amino-naphthalene, 1-amino-4-methyl-naphthalene, 2-amino-1-methyl-naphthalene and 1-amino-2-methyl-naphthalene.

The compounds which follow are preferably reacted with the abovementioned arylamines under the conditions according to the invention to give the arylthioureas II: thiocyanic acid (for carrying out the reaction with thiocyanic acid see Houben Weyl "Methoden der Organischen Chemie" ("Methods of Organic Chemistry"), Georg Thieme Verlag Stuttgart 1955, Volume 9, page 888), methyl isothiocyanate and ethyl isothiocyanate.

The reaction is carried out in the solvents and concentrations claimed according to the invention and at temperatures of 20°–120° C., preferably 40°–80° C.

Alternatively, it is also possible to react the aryl isothiocyanates from the arylamines listed as examples above with, preferably, ammonia, methylamine or ethylamine under otherwise identical reaction conditions to give the same arylthioureas II.

The preparation of the aryl isothiocyanates from the arylamines can be carried out by reaction with thiophosgene in water/chloroform or water/dichloroethane mixtures, with the addition of calcium carbonate, at temperatures of 20°–80° C., or by reacting the N-aryldithiocarbamates with oxidising agents, such as hypochlorite solution, or acid chlorides, such as phosgene (see Houben-Weyl "Methoden der Organischen Chemie" ("Methods of Organic Chemistry"), Georg Thieme Verlag Stuttgart 1955, Volume 9, page 867 et seq.).

The following may be listed as examples of N-arylthioureas and N-aryl-N'-alkyl-thioureas of the general formula II which are formed as intermediate products in the process claimed: N-(2-methyl-phenyl)-thiourea, N-(2-methyl-phenyl)-N'-methyl-thiourea, N-(2-methyl-phenyl)-N'-ethyl-thiourea, N-(4-methyl-phenyl)-N'-methyl-thiourea, N-(2,4-dimethyl-phenyl)-thiourea, N-(2,4-dimethyl-phenyl)-N'-methyl-thiourea, N-(2,4-dimethyl-phenyl)-N'-ethyl-thiourea, N-(2,3-dimethyl-phenyl)-N'-methyl-thiourea, N-(2,6-dimethyl-phenyl)-N'-methyl-thiourea, N-(2-methyl-4-ethyl-phenyl)-N'-methyl-thiourea, N-(4-methyl-2-ethyl-phenyl)-N'-methyl-thiourea, N-(2-methyl-3-ethyl-phenyl)-N'-methyl-thiourea, N-(3-methyl-2-ethyl-phenyl)-N'-methyl-thiourea, N-(2-methyl-6-ethyl-phenyl)-N'-methyl-thiourea, N-(2-ethyl-phenyl)-Thiourea, N-(2-ethyl-phenyl)-N'-methyl-thiourea, N-(2-ethyl-phenyl)-N'-ethyl-thiourea, N-(2,6-diethyl-phenyl)-thiourea, N-(2,6-diethyl-phenyl)-N'-methyl-thiourea, N-(2,6-diethyl-phenyl)-N'-ethyl-thiourea, N-(2,4-diethyl-phenyl)-N'-methyl-thiourea, N-(2,4,5-trimethyl-phenyl)-N'-methyl-thiourea, N-(2,3,4-trimethyl-phenyl)-N'-methyl-thiourea, N-(2,4,6-trimethyl-phenyl)-N'-methyl-thiourea, N-(2,3,6-trimethyl-phenyl)-N'-methyl-thiourea, N-(2-isopropyl-phenyl)-N'-methyl-thiourea, N-(2-ethyl-4,5-dimethyl-phenyl)-N'-methyl-thiourea, N-(2-chloro-phenyl)-N'-methyl-thiourea, N-(2,3-dichloro-phenyl)-N'-methyl-thiourea, N-(3,4-dichloro-phenyl)-N'-methyl-thiourea, N-(2,6-dichloro-phenyl)-N'-methyl-thiourea, N-(2,4,6-trichloro-phenyl)-N'-methyl-thiourea, N-(pentachloro-phenyl)-N'-methyl-thiourea, N-(2-methyl-4-chloro-phenyl)-thiourea, N-(2-methyl-4-chlorophenyl)-N'-methyl-thiourea, N-(2-methyl-4-chloro-phenyl)-N'-ethyl-thiourea, N-(3-chloro-4-methyl-phenyl)-N'-methyl-thiourea, N-(2-chloro-3-methyl-phenyl)-N'-methyl-thiourea, N-(2-chloro-6-methyl-phenyl)-N'-methyl-thiourea, N-(3-chloro-2-methyl-phenyl)-N'-methyl-thiourea, N-(5-chloro-2,4-dimethyl-phenyl)-N'-methyl-thiourea, N-(4-chloro-2,5-dimethyl-phenyl)-N'-methyl-thiourea, N-(2-chloro-4-trifluoromethyl-phenyl)-N-methyl-thiourea, N-(3,5-bis-trifluoromethyl-phenyl)-N'-methyl-thiourea, N-(4-biphenylyl)-N'-methyl-thiourea, N-(4-hydroxy-phenyl)-N'-methyl-thiourea, N-(2-chloro-4-methoxy-phenyl)-N'-methyl-thiourea, N-(2,4-dimethoxy-phenyl)-N'-methyl-thiourea, N-(3,5-dichloro-4-(4'-chloro-phenoxy)-phenyl)-N'-methyl-thiourea, N-(3,5-dichloro-4-(4'-chloro-phenoxy)-phenyl)-thiourea, N-(4-amino-phenyl)-N'-methyl-thiourea, N-(4-dimethylamino-phenyl)-N'-methyl-thiourea, N-(4-anilino-phenyl)-N'-methyl-thiourea, N-(1-naphthyl)-N'-methyl-thiourea, N-(1-chloro-naphthyl-2)-N'-methyl-thiourea and N-(4-methyl-naphthyl-1)-N'-methyl-thiourea.

The N-aryl thioureas of the general formula II listed as examples above are reacted, under the conditions claimed according to the invention and without intermediate isolation, with a 2-halogeno-carbonyl compound of the general formula III

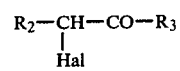

wherein

R$_2$, R$_3$ and Hal have the meaning indicated above, or with an acetal derivative of a compound of the general formula III. The following may be listed as examples of compounds III: chloroacetaldehyde, methyl (1,2-dichloro-ethyl) ether, ethyl (1,2-dichloro-ethyl) ether, methyl (1,2-dichloro-propyl) ether, 2-chloro-propionaldehyde, chloroacetaldehyde diethyl acetal, bromoacetaldehyde dimethyl acetal, 2-chloromethyl-1,3-dioxolane, monochloroacetone, 3-chloro-2-butanone and 1-chloro-2-butanone.

The halogenocarbonyl compounds listed above or their equivalents are slowly added to the suspensions of the N-aryl-thioureas II in equimolar amounts or in a slight excess (for example 1–10%) at temperatures from 20°–120° C., preferably 40°–80° C. Thereafter, the mixture is allowed to react in the same temperature range until the N-aryl-thiourea II can no longer be detected. In most cases the suspension becomes liquid during this procedure since the 2-arylimino-thiazolines I have lower boiling points and a substantially better solubility in the solvents used according to the claims than the N-aryl-thioureas II. In some cases it can be advantageous to add small amounts of water to the mixtures, for example 5–50% of the total volume.

After the cyclization reaction has ended, the acid formed is neutralised by adding an aqueous base, such as sodium carbonate solution, potassium carbonate solution, sodium hydroxide solution or dilute ammonia solution. Thereafter, the aqueous phase is separated off and the organic phase is dried with a drying agent (potassium carbonate or anhydrous sodium sulphate) or by distilling off the low-boiling auxiliary solvent which is optionally simultaneously used (boiling point preferably below 100° C.).

Solutions of the 2-arylamino-thiazolines I are thus obtained in a concentration range which is appropriate for finishing the formulations.

The yields of 2-arylimino-thiazolines I are very good (over 90% of theory); by-products cannot be detected or can only be detected in minor amounts.

The following may be mentioned as examples of 2-aryl-imino-thiazolines of the general formula I which can be prepared by the process claimed: 2-phenylamino-3-methyl-thiazoline, 2-(2-methyl-phenylamino)-thiazoline, 2-(2-methylphenylimino)-3-methyl-thiazoline, 2-(2-methyl-phenylamino)-3-ethyl-thiazoline, 2-(4-methyl-phenylimino)-3-methyl-thiazoline, 2-(2,4-dimethyl-phenylimino)-thiazoline, 2-(2,4-dimethyl-phenylimino)-3-methyl-thiazoline, 2-(2,4-dimethyl-phenylimino)-4-methyl-thiazoline, 2-(2,4-dimethyl-phenylimino)-5-methylthiazoline, 2-(2,4-dimethyl-phenylimino)-3,4-dimethyl-thiazoline, 2-(2,4-dimethyl-phenylimino)-3,5-dimethyl-thiazoline, 2-(2,4-dimethyl-phenylimino)-4,5-dimethyl-thiazoline, 2-(2,4-dimethyl-phenylimino)-5-ethyl-thiazoline, 2-(2,4-dimethyl-phenylimino)-3-ethyl-thiazoline, 2-(2,4-dimethylphenylimino)-3-methyl-5-ethyl-thiazoline, 2-(2,3-dimethylphenylimino)-3-methyl-thiazoline, 2-(2,6-dimethyl-phenylimino)-3-methyl-thiazoline, 2-(2-methyl-4-ethyl-phenylimino)-3-methyl-thiazoline, 2-(4-methyl-2-ethyl-phenylimino)-3-methyl-thiazoline, 2-(2-methyl-6-ethyl-phenylimino)-3-methyl-thiazoline, 2-(2-methyl-3-ethyl-phenylimino)-3-methyl-thiazoline, 2-(3-methyl-2-ethyl-phenylimino)-3-methyl-thiazoline, 2-(2-ethylphenylimino)-thiazoline, 2-(2-ethyl-phenylimino)-3-methyl-thiazoline, 2-(2-ethyl-phenylimino)-3,5-dimethyl-thiazoline, 2-(2,6-diethyl-phenylimino)-thiazoline, 2-(2,6-diethyl-phenylimino) 2-(2,6-diethyl-phenylimino)-5-methyl-thiazoline, 2-(2,6-diethyl-phenylimino)-3-ethylthiazoline, 2-(2,6-diethyl-phenylamino)-3,5-dimethylthiazoline, 2-(2,4-diethyl-phenylimino)-3-methyl-thiazoline, 2-(2,4,5-trimethyl-phenylminino)-3-methyl-thiazoline, 2-(2,3,4-trimethyl-phenylimino)-3-methyl-thiazoline, 2-(2,4,6-trimethyl-phenylimino)-3-methyl-thiazoline, 2-(2,3,6-trimethyl-phenylimino)-3-methyl-thiazoline, 2-(2-isopropyl-phenylimino)-3-methyl-thiazoline, 2-(2-ethyl-4,5-dimethyl-phenylimino)-3-methyl-thiazoline, 2-(2-chloro-phenylimino)-3-methyl-thiazoline, 2-(2,3-dichloro-phenylimino)-3-methyl-thiazoline, 2-(3,4-dichloro-phenylimino)-3-methyl-thiazoline, 2-(2,6-dichlorophenylimino)-3-methyl-thiazoline, 2-(2,4,6-trichloro-phenylimino)-3-methyl-thiazoline, 2-(pentachlorophenylimino)-3-methyl-thiazoline, 2-(2-methyl-4-chloro-phenylimino)-thiazoline, 2-(2-methyl-4-chloro-phenylimino)-3-methyl-thiazoline, 2(2-methyl-4-chloro-phenylimino)-5-methyl-thiazoline, 2-(2-methyl-4-chloro-phenylimino)-3,5-dimethyl-thiazoline, 2-(2-methyl-4-chloro-phenylimino)-3,4,5-trimethyl-thiazoline, 2-(2-methyl-4-chloro-phenylimino)-3-methyl-5-ethyl-thiazoline, 2-(2-methyl-4-chloro-phenylimino)-3-ethyl-thiazoline, 2-(3-chloro-4-methylphenylimino)-3-methyl-thiazoline, 2-(2-chloro-3-methyl-phenylimino)-3-methyl-thiazoline, 2-(2-chloro-6-methyl-phenylimino)-3-methyl-thiazoline, 2-(3-chloro-2-methyl-phenylimino)-3-methyl-thiazoline, 2-(5-chloro-2,4-dimethyl-phenylimino)-3-methyl-thiazoline, 2-(4-chloro-2,5-dimethyl-phenylimino)-3-methyl-thiazoline, 2-(2-chloro-4-trifluoromethyl-phenylimino)-3-methyl-thiazoline, 2-(3,5-bis-trifluoromethyl-phenylimino)-3-methyl-thiazoline, 2-(4-biphenylylimino)-3-methyl-thiazoline, 2-(4-hydroxy-phenylimino)-3-methyl-thiazoline, 2-(3-hydroxyphenylimino)-thiazoline, 2-(2-chloro-4-methoxy-phenylimino)-3-methyl-thiazoline, 2-(2,4-dimethoxy-phenylimino)-3-methylthiazoline, 2-(3,5-dichloro-4-(4'-chloro-phenoxy)-phenylimino)thiazoline, 2-(3,5-dichloro-4-(4'-chlorophenoxy)-phenylimino)-3-methyl-thiazoline, 2-(4-aminophenylimino)-3-methylthiazoline, 2-(4-aminophenylimino)-thiazoline, 2-(4-aminophenylimino)-3,5-dimethyl-thiazoline, 2-(4-amino-phenylimino)-4-methyl-thiazoline, 2-(4-dimethylamino-phenylimino)-3-methylthiazoline, 2-(4-anilino-phenylimino)-3-methyl-thiazoline, 2-(1-naphthylimino)-3-methyl-thiazoline, 2-(1-chloro-2-naphthylimino)-3-methyl-thiazoline and 2-(4-methyl-1-naphthylimino)-3-methyl-thiazoline.

The examples which follow are intended to document the preparation of the aryliminothiazolines by the process according to the invention.

EXAMPLE 1

2-(2,4-Dimethyl-phenylimino)-3-methyl-thiazoline 400 g of 4-amino-1,3-dimethyl-benzene and 400 g of solvent consisting of a mixture of alkylaromatic compounds having a boiling point of about 250° C. (solvent HAN) and 200 ml of cyclohexane are initially introduced at 40° C. and 255 g of methyl isothiocyanate are added dropwise in the course of 15 minutes. The temperature is allowed to rise to 80° C. during this addition and crystallisation of the N-(2,4-dimethylphenyl)-N'-methyl-thiourea formed is initiated by seeding. As soon as the diazotisation test shows the absence of aromatic amines, 630 g of chloroacetaldehyde (45% strength aqueous solution) are allowed to run into the mixture in the course of 20–30 minutes at an initial temperature of 80° C. The mixture is cooled so that the temperature does not exceed 80° C. The thiourea goes into solution during this procedure and a liquid emulsion is formed. The emulsion is kept at 80° C. for a further 1 hour and 700 ml of 23% strength sodium carbonate solution are then allowed to run in in the course of about 1 hours. The internal temperature falls to about 30° C. After settling, the lower aqueous phase is run off and the uper solution phase is freed from cyclohexane and moisture at 80°–85° C./15–20 mm Hg. Yield 1,100 g; according to analysis by gas chromatography, a 62% strength solution of 2-(2,4-dimethyl-phenylimino)-3-methyl-thiazoline in a mixture of alkylaromatic compounds is present (yield 95% of theory).

Instead of cyclohexane, it is also possible to use benzene or toluene as the auxiliary solvent; instead of a mixture of alkylaromatic compounds, it is also possible to use orthodichlorobenzene or xylene, anisole, diphenyl ether or diphenyl ether/diphenyl mixtures as the solvent.

The determination of the content of active compound in the solution prepared as above is carried out with a PerkinElmer F 20 (FJD) gas chromatograph; column 1.5 m; 5% Apiezon L, 5% KOH on Chromosorb WHP; 80–100 mesh. Condition: 200° C.; injection 0.2 microlitre. The determination is carried out using 4-(N-isopropylamino)-diphenylamine as the internal standard and in the form of a 10% strength solution in chloroform. 5.0 ml of standard solution are added to 1.0 g of the active compound solution according to the above preparation example and the mixture is injected in this form. The evaluation of the result is carried out using a computer PRAG 320. The determination of the correction factor is carried out in the same manner using a pure sample of 2-(2,4-dimethyl-phenylimino)-3-methyl-thiazoline. This comparison sample is prepared as follows:

100 g of N-(2,4-dimethyl-phenyl)-N'-methyl-thiourea are suspended in 400 ml of acetone and 90 g of a 45% strength aqueous solution of chloroacetaldehyde are added dropwise at 10° C. to 15° C. Thereafter, the mixture is heated to the reflux for 2 hours and the acetone is then substantially distilled off. The residue is stirred with 1.5 l of water and 50 ml of 45% strength sodium hydroxide solution, the oily reaction product is taken up in methylene chloride and the methylene chloride solution is dried over potassium carbonate and fractionated: boiling point 145°–150° C./0.5 mm Hg, yield 96 g; 86% of theory. The compound crystallises on seeding or standing for a long time; melting point: 42°–43° C. from petroleum ether.

The abovementioned N-(2,4-dimethyl-phenyl)-N'-methylthiourea used as the starting compound can be prepared in the following manner:

200 g of 4-amino-1,3-dimethylbenzene are dissolved in 200 ml of dioxane and 100 ml of triethylamine and 124 g of methyl isothiocyanate are added. When the exothermic reaction has ended and the detection of the amine by means of a diazotisation reaction has a negative result, the mixture is diluted with 1 l of warm water and 500 ml of acetic acid and the reaction product is filtered off and washed with water and methanol.

Yield: 282 g; 90% of theory; melting point: 150°–152° C.

EXAMPLE 2

2-(2,6-Diethyl-phenylimino)-3-methyl-thiazoline 300 g of 2-amino-1,3-diethylbenzene are dissolved in 440 g of 1-chloronaphthalene and 600 ml of benzene at 40° C. and 153 g of methyl isothiocyanate is added dropwise in the course of 15 minutes. The temperature is allowed to rise to about 70° C. When the detection of aromatic amine by means of a diazotisation reaction gives a negative result, the dropwise addition of a total of 385 g of chloroacetaldehyde (45% strength aqueous solution) is started. The thiourea which has crystallised out goes into solution during this procedure. The mixture is kept at 70° C. for a further 1 hour and a solution of 140 g of sodium carbonate in 700 ml of water is then allowed to run in. After cooling and settling, the aqueous phase is separated off. Thereafter, the benzene is distilled off from the organic phase up to 70° C./15 mm Hg. 910 g of a 52% strength solution of the thiazoline derivative in 1-chloronaphthalene are obtained; yield: 96% of theory.

If 195 g of monochloroacetone are used in the above example instead of chloroacetaldehyde and the procedure followed is as indicated, a 54% strength solution of 2-(2,6-diethylphenylimino)-3,4-dimethyl-thiazoline is obtained in 95% yield.

The determination of the content of pure compound in the resulting active compound solutions is carried out by gas chromatography according to the process described in Example 1.

EXAMPLE 3

2-(2-Ethyl-phenylimino)-3-methyl-thiazoline 300 g of 2-amino-1-ethylbenzene are dissolved in 260 g of 1,2,4-trichlorobenzene and 800 ml of methylene chloride at 40° C. and 190 g of methyl isothiocyanate are added dropwise, whilst cooling. When the detection of the aromatic amine gives a negative result, 470 g of a 45% strength aqueous solution of chloroacetaldehyde are added dropwise to the suspension of the thiourea. The thiourea goes into solution. The mixtue is stirred for a further 2 hours at 60° C. and the absence of N-(2-ethylphenyl)-N'-methyl-thiourea is checked by chromatography. Thereafter, a solution of 200 g of potassium carbonate in 1,000 ml of water is allowed to run in, the organic layer is separated off and the methylene chloride is distilled off up to 60° C./15 mm Hg. Yield: 760 g of a 66% strength solution of 2-(2-ethylphenylimino)-3-methyl-thiazoline in 1,2,4-trichlorobenzene; yield: 93% of theory.

The determination of the content of pure compound in the resulting active compound solutions is carried out by gas chromatography according to the process described in Example 1

EXAMPLE 4

2-(2,4-Dimethyl-phenylimino)-3-methyl-thiazoline 39 g of methylamine are passed into a solution of 200 g of 2,4-dimethyl-phenyl isothiocyanate in 860 g of a mixture of alkylaromatic compounds having an average boiling point of 250° C. (solvent HAN) at 15°–20° C. The mixture is subsequently stirred for a further 2 hours and 240 g of a 45% strength aqueous solution of chloroacetaldehyde are then added dropwise. Thereafter, the mixture is stirred for a further 2 hours at 60° C. and a solution of 75 g of sodium carbonate in 500 ml of water is then allowed to run in. The organic layer is separated off and dried by stirring with potassium carbonate and filtration. Yield 1,001 g of a 24% strength solution of 2-(2,4-dimethyl-phenylimino)-3-methyl-thiazoline in a mixture of alkylaromatic compounds; yield: 90% of theory.

If 2,4-dimethyl-phenyl isothiocyanate in the above example is replaced by the same amount of 2,3-dimethyl-phenyl isothiocyanate and the procedure followed is an indicated, a solution of 2-(2,3-dimethyl-phenylimino)-3-methyl-thiazoline is obtained in a similar concentration and yield.

If methylamine in the above example is replaced by equivalent amounts of ammonia or allylamine, solutions of 2-(2,4-dimethyl-phenylimino)-thiazoline or, respectively, 2-(2,4-dimethyl-phenylimino)-3-allyl-thiazoline are obtained.

The determination of the content of pure compound in the resulting active compound solutions is carried out by gas chromatography according to the process described in Example 1.

EXAMPLE 5

2-(2,4,5-Trimethyl-phenylimino)-3-methyl-thiazoline 300 g of 5-amino-1,2,4-trimethyl-benzene are dissolved in 400 g of triisopropylbenzene (mixture of isomers) and 800 ml of chloroform and 240 g of methyl isothiocyanate are added dropwise. When the detection of aromatic amine gives a negative result, 435 g of a 45% strength aqueous solution of chloroacetaldehyde are added dropwise and the mixture is warmed to 60° C. for 2 hours. Thereafter, 1,250 ml of 2 N sodium hydroxide solution are added dropwise. The mixture is cooled to 10°–15° C., the organic phase is separated off and the chloroform is distilled off up to 60° C./15 mm Hg. Yield 885 g of a 55% strength solution of 2-(2,4,5-trimethyl-phenylimino)-3-methyl-thiazoline; yield: 94% of theory.

If 5-amino-1,2,4-trimethylbenzene in the above example is replaced by the same amount of 4-amino-1,2,3-trimethylbenzene, a solution of 2-(2,3,4-trimethyl-phenylimino)-3-methyl-thiazoline is obtained.

If 5-amino-1,2,4-trimethyl-benzene in the above example is replaced by 320 g of 1-amino-naphthalene and the procedure followed is as indicated, a solution of 2-(1-naphthyl-imino)-3-methyl-thiazoline is obtained.

If chloroacetaldehyde in the above example is replaced by 226 g of 2-chloro-propionaldehyde and the procedure followed is as indicated, a solution of 2-(2,4,5-trimethyl-phenylimino)-3,5-dimethyl-thiazoline is obtained.

The determination of the content of pure compound in the resulting active compound solutions is carried out by gas chromatography according to the process described in Example 1.

I claim:

1. Process for the preparation of solutions containing, in a yield of at least 90%, 2-aryliminothiazolines of the formula

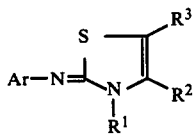

in which
Ar represents phenyl or naphthyl which is unsubstituted or substituted by
alkyl ($C_1$–$C_4$), halogen,
trifluoromethyl, amino, dialkylamino ($C_1$–$C_4$) per alkyl group, alkanoylamino ($C_1$–$C_4$) and alkoxycarbonylamino ($C_1$–$C_4$), cycloalkyl ($C_3$–$C_6$), alkoxy ($C_1$–$C_4$), phenyl, phenoxy, alkylsulphonyl ($C_1$–$C_4$), nitro, cyano, or alkanoyl ($C_1$–$C_4$) or a combination of said substituents and
$R^1$, $R^2$ and $R^3$ independently of one another represent hydrogen or alkyl ($C_1$–$C_4$),
which comprises reacting
(a) either an arylamine of the formula Ar-NH$_2$ in which
Ar has the meaning indicated above with a compound of the formula $R^1$-NCS in which
$R^1$ represents hydrogen or alkyl ($C_1$–$C_4$), then reacting the thiourea intermediate product formed, without isolation, with a halogenocarbonyl compound of the formula

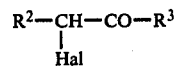

in which
$R^2$ and $R^3$ have the meaning indicated above and
Hal represents halogen, or with an acetal of the abovementioned 2-halogenocarbonyl compound III, in an aromatic solvent or mixture of solvents of the benzene or naphthalene series, the boiling range of which is between 130° and 400° C., at a temperature between about 20° and about 120° C. and then separating the aqueous phase from the reaction mixture to provide a solution of the 2-arylimino-thiazoline in the aromatic solvent of the benzene or naphthalene series (boiling range 130° to 400° C.), or which comprises reacting
(b) an aryl isocyanate of the formula Ar-NCS in which
Ar has the meaning indicated above, with a compound of the formula $R^1$-NH$_2$ in which
$R^1$ represents hydrogen or alkyl ($C_1$–$C_4$), then reacting the thiourea intermediate product formed, without isolation, with a halogenocarbonyl compound of the formula

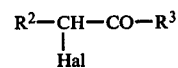

in which
$R^2$ and $R^3$ have the meaning indicated above and
Hal represents halogen, or with an acetal of the abovementioned 2-halogenocarbonyl compound III, in an aromatic solvent of the benzene or naphthalene series, the boiling range of which is between 130° and 400° C., at temperatures between about 20° and about 120° C. and then separating the aqueous phase from the reaction mixture to provide a solution of the 2-aryliminothiazoline in the aromatic solvent of the benzene or naphthalene series (boiling range 130° to 400° C.).

2. Process according to claim 1, wherein the aromatic solvent (boiling range 130° to 400° C.) is used in such an amount that after the reaction has been carried out about 10–80% strength solutions of the 2-aryliminothiazolines of the formula I are present.

3. Process according to claim 1 wherein Ar represents a phenyl or naphthyl radical substituted by alkyl ($C_1$–$C_4$), halogen, trifluoromethyl, amino, dialkylamino ($C_1$–$C_4$) per alkyl group, alkanoylamino ($C_1$–$C_4$) and alkoxycarbonylamino ($C_1$–$C_4$), cycloalkyl ($C_3$–$C_6$), alkoxy ($C_1$–$C_4$), phenyl, phenoxy, alkylsulphonyl ($C_1$–$C_4$), nitro, cyano, or alkanoyl ($C_1$–$C_4$).

4. Process according to claim 1, wherein a solvent which is immiscible with water and has a boiling point below 100° C. is employed as a further solvent in addition to the aromatic solvent (boiling range 130° to 400° C.).

5. Process according to claim 4 wherein the solvent which is immiscible with water is an aliphatic hydrocarbon.

* * * * *

UNITED STATES PATENT AND TRADEMARK OFFICE
CERTIFICATE OF CORRECTION

PATENT NO. : 4,148,799            Page 1 of 2
DATED : April 10, 1979
INVENTOR(S) : Edgar Enders It is certified that error appears in the above-identified patent and that said Letters Patent are hereby corrected as shown below:

Column 9, line 24, "phenylamino-" should be --phenylimino--.

Column 9, line 25, "phenylamino-" should be --phenylimino--.

Column 9, line 27, "phenylamino-" should be --phenylimino--.

Column 9, lint 51, "phenylamino-" should be --phenylimino--.

Column 9, line 53, "phenylminino" should be --phenylimino--.

Column 9, line 66, "2(2 " should be --2-(2--.

Column 10, line 4, insert " - " after "methyl".

UNITED STATES PATENT AND TRADEMARK OFFICE
CERTIFICATE OF CORRECTION

PATENT NO. : 4,148,799
DATED : April 10, 1979
INVENTOR(S) : Edgar Enders

It is certified that error appears in the above-identified patent and that said Letters Patent are hereby corrected as shown below:

Column 10, line 17, insert "-" after "methyl"

Column 10, line 22, insert "-" after "amino"

Column 10, line 54, "hours" should be --hour--.

Column 11, line 3, insert "-" after "Perkin".

Column 12, line 56, "an" should be --as--.

Signed and Sealed this

Ninth Day of October 1979

[SEAL]

Attest:

RUTH C. MASON
Attesting Officer

LUTRELLE F. PARKER
Acting Commissioner of Patents and Trademarks